US008653830B2

(12) United States Patent
Maxey et al.

(10) Patent No.: US 8,653,830 B2
(45) Date of Patent: Feb. 18, 2014

(54) OPTICALLY STIMULATED DIFFERENTIAL IMPEDANCE SPECTROSCOPY

(75) Inventors: Lonnie C. Maxey, Powell, TN (US);
James E. Parks, II, Knoxvile, TN (US);
Samuel A. Lewis, Sr., Powell, TN (US);
William P Partridge, Jr., Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 1058 days.

(21) Appl. No.: 12/326,223

(22) Filed: Dec. 2, 2008

(65) Prior Publication Data

US 2012/0182025 A1 Jul. 19, 2012

(51) Int. Cl.
*G01R 27/02* (2006.01)

(52) U.S. Cl.
USPC ........... 324/603; 324/602; 324/609; 324/658; 324/660; 324/698

(58) Field of Classification Search
CPC .... G01R 27/02; G01R 27/22; G01R 27/2635; G01R 27/2641; G01R 27/2682
USPC .................. 324/603, 602, 609, 658, 660, 698
See application file for complete search history.

(56) References Cited

U.S. PATENT DOCUMENTS

| 5,843,783 | A * | 12/1998 | Rutledge et al. ................ 436/56 |
| 7,106,075 | B2 * | 9/2006 | Hu ................................ 324/698 |
| 7,291,824 | B2 * | 11/2007 | Kiesel et al. ................ 250/208.2 |
| 7,315,767 | B2 * | 1/2008 | Caduff et al. ................ 700/266 |
| 7,839,492 | B2 * | 11/2010 | Parks et al. ..................... 356/70 |
| 7,877,009 | B2 * | 1/2011 | Wang et al. ....................... 398/9 |
| 2002/0121529 | A1 * | 9/2002 | Hoummady ................... 222/113 |
| 2003/0072549 | A1 * | 4/2003 | Facer et al. .................... 385/129 |
| 2004/0201835 | A1 * | 10/2004 | Coates et al. .................. 356/73 |
| 2005/0088646 | A1 * | 4/2005 | Kong et al. ..................... 356/70 |
| 2006/0175192 | A1 * | 8/2006 | Lin ............................... 204/194 |
| 2008/0204048 | A1 * | 8/2008 | Stasiak et al. ................. 324/679 |
| 2009/0054908 | A1 * | 2/2009 | Zand et al. ..................... 606/130 |
| 2009/0162076 | A1 * | 6/2009 | Wang et al. ..................... 398/185 |
| 2012/0019829 | A1 * | 1/2012 | Parks et al. .................... 356/437 |
| 2012/0114089 | A1 * | 5/2012 | Potyrailo et al. .............. 376/247 |
| 2013/0204488 | A1 * | 8/2013 | Von Herzen et al. ........ 701/34.4 |

OTHER PUBLICATIONS

Jansen and Orazem, Identification of Deep-Level States in Electronic Materials by Optically Stimulated Deep-Level Impedance Spectroscopy, May 1992, J. Electrochem. Soc., vol. 139, No. 5.*
Jansen and Orazem, Optically Stimulated Deep-Level Impedance Spectroscopy, Dec. 1996, J. Electrochem. Soc., vol. 143, No. 12.*

(Continued)

*Primary Examiner* — Patrick J Assouad
*Assistant Examiner* — Adam Clarke
(74) *Attorney, Agent, or Firm* — Luedeka Neely Group, P.C.

(57) ABSTRACT

Methods and apparatuses for evaluating a material are described. Embodiments typically involve use of an impedance measurement sensor to measure the impedance of a sample of the material under at least two different states of illumination. The states of illumination may include (a) substantially no optical stimulation, (b) substantial optical stimulation, (c) optical stimulation at a first wavelength of light, (d) optical stimulation at a second wavelength of light, (e) a first level of light intensity, and (f) a second level of light intensity. Typically a difference in impedance between the impedance of the sample at the two states of illumination is measured to determine a characteristic of the material.

19 Claims, 11 Drawing Sheets

(56) References Cited

OTHER PUBLICATIONS

Mark E. Orazem, Pankaj Agarwal, and Luis H. Garcia-Rubio Critical issues associated with interpretation of impedance spectra J. of Electroanalytical Chemistry vol. 378 pp. 51-62 Apr. 25, 1994.*

Gamry Instruments, "Basics of Electrochemical Impedance Spectroscopy", Copyright 2007 Rev. 5, Gamry Instruments, 734 Louis Drive, Warminster, PA 18974.

* cited by examiner

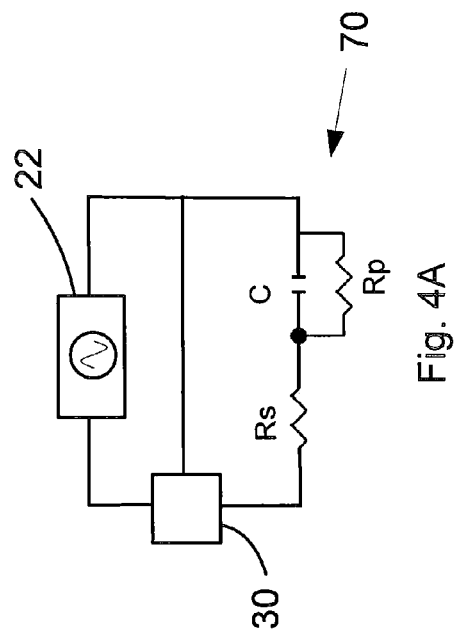
Fig. 3
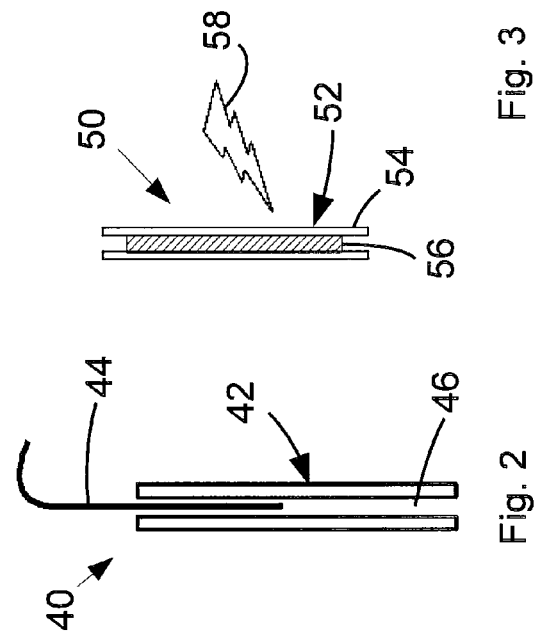
Fig. 2
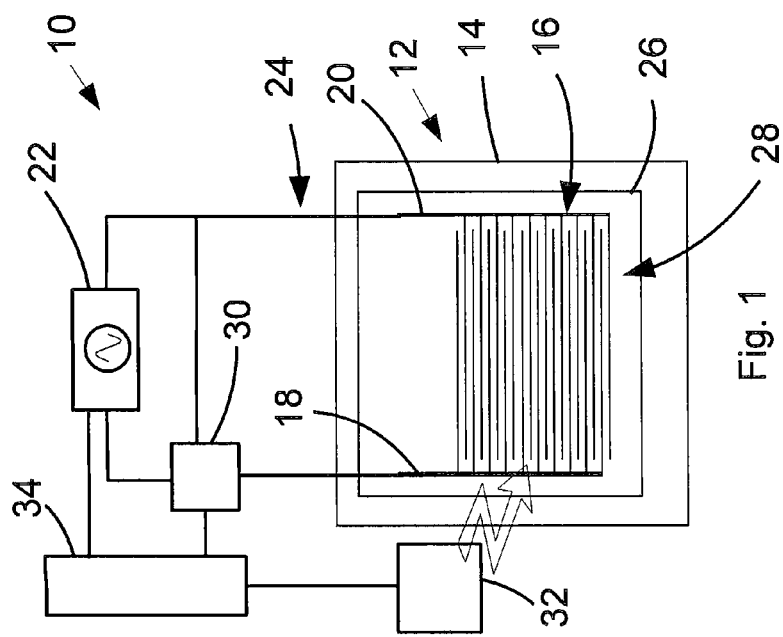
Fig. 4A
Fig. 1

US 8,653,830 B2

OPTICALLY STIMULATED DIFFERENTIAL IMPEDANCE SPECTROSCOPY

GOVERNMENT RIGHTS

This invention was made with government support under Contract No. DE-AC05-00OR22725 awarded by the U.S. Department of Energy. The government has certain rights in the invention.

FIELD

This disclosure relates to the field of electrical impedance spectroscopy. More particularly, this disclosure relates to electrical impedance spectroscopy combined with optical illumination.

BACKGROUND

In recent years, Electrical Impedance Spectroscopy (EIS) has become an important tool in analytical chemistry. EIS is typically used for analyzing the condition of solid state devices, batteries, fuel cells and liquid chemical samples. For electrochemical analysis of liquid samples, EIS is typically performed by placing a capacitive electrode into the sample to be measured. The liquid becomes the dielectric in the capacitive electrode and the variation in impedance, as a function of frequency, reveals information about the electrochemical properties of the sample. This information typically pertains to a chemical, physical, or electrical property of the sample.

It is highly preferable when performing EIS analysis of a material sample that the impedance-based measurement varies monotonically with variations in the chemical, physical or electrical property of the sample that is being evaluated. It is also preferable that the impedance-based measurement reveals quantitative information about the property of the sample. Unfortunately conventional EIS analysis does not always produce these preferable characteristics. What are needed therefore are improved systems and processes for electrical impedance spectroscopy.

SUMMARY

In one embodiment the present disclosure provides a method of evaluating a material that typically includes a step of measuring a first electrical impedance of the material under a first state of illumination, and a further step of measuring a second electrical impedance of the material under a second state of illumination that is different from the first state of illumination. The method typically further typically includes evaluating the material based upon a difference between the first electrical impedance and the second electrical impedance.

Also provided is an apparatus for evaluating a material. The apparatus typically includes an impedance sensor system that is configured to measure impedance of the composition of material. Further included, typically, is a source of optical stimulation configured to expose the material to at least two different states of illumination, and a control system that is configured to (1) switch the source of optical stimulation between the at least two different states of illumination, and (2) trigger the impedance sensor system to measure the impedance of the material at each of the at least two different states of illumination.

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein:

FIG. 1 is a somewhat schematic plan view illustration of a device for measuring the impedance of a composition of material.

FIGS. 2 & 3 are somewhat schematic cross sectional illustrations of devices for measuring the impedance of a composition of material.

FIG. 4A is an electrical schematic that includes a circuit that is substantially an electrical equivalent of an electrode and chemical sample arrangement in a typical electrochemical impedance measurement system.

DETAILED DESCRIPTION

Figure 4C:
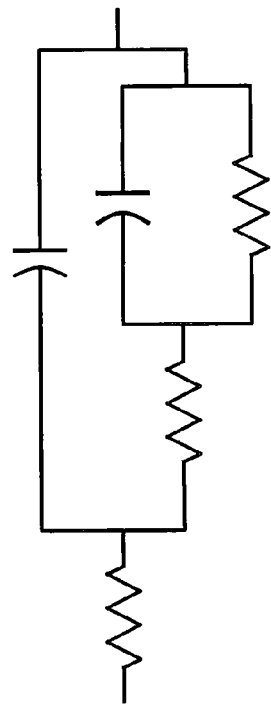
FIGS. 4B-4E depict circuits that are electrical equivalents of some electrode and chemical sample arrangements in electrochemical impedance measurement systems.
Figure 4E:
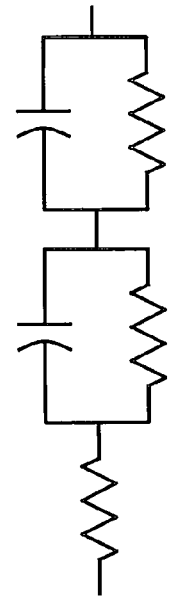
Figure 4B:
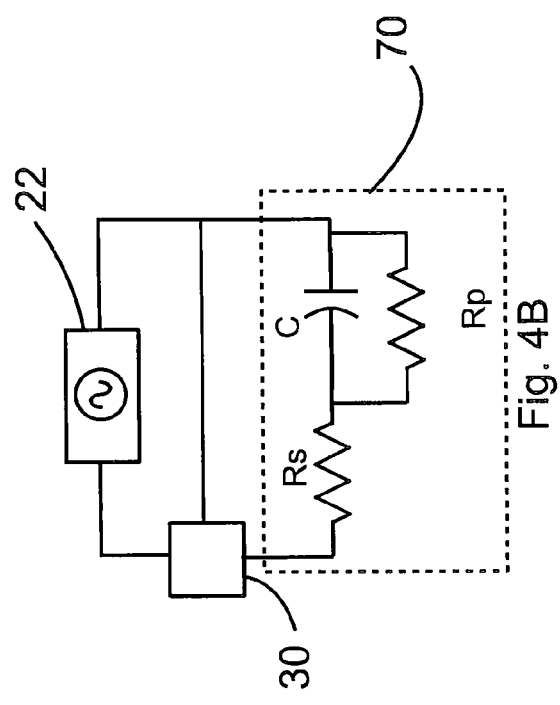
Figure 4D:
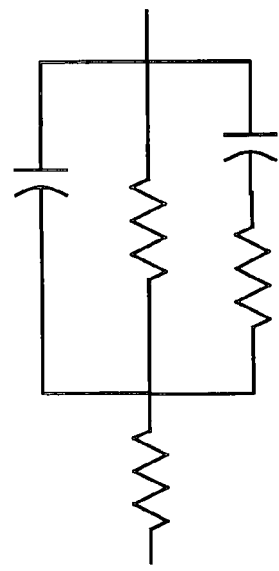

In the following detailed description of the preferred embodiments, reference is made to the accompanying drawings, which form a part hereof, and within which are shown by way of illustration the practice of specific embodiments of methods of evaluating a composition of material and embodiments of apparatuses for evaluating a composition of material. It is to be understood that other embodiments may be utilized, and that structural changes may be made and processes may vary in other embodiments.

One embodiment of an apparatus 10 for evaluating a composition of material is illustrated in FIG. 1. The apparatus 10 permits optical measurements of materials that are substantially opaque. The apparatus 10 includes impedance sensor 12. The impedance sensor 12 includes a printed circuit board 14 that includes a pattern of interdigitated electrodes 16. The interdigitated electrodes 16 provide an electrical capacitance that ranges in air from a fraction of a picofarad to a few microfarads, and particularly ranges from about 1 pF to about 10 pF, with about 7 pF being an exemplary value. Approximately half of the interdigitated electrodes 16 are electrically connected to a first terminal 18 and the remaining portion of the interdigitated electrodes 16 are connected to a second terminal 20. The impedance sensor 12 further includes a voltage source 22 that is connected across the first terminal 18 and the second terminal 20. The voltage source 22 is typically configured to provide a voltage at variable frequencies ranging from close to direct current (DC) (typically 1 Hz) to several megahertz and particularly ranging from about 1 Hz to about 3 MHz. The peak-to peak or DC voltage may be set to range from a few millivolts to a few volts, and in particular the amplitude of AC sweeps is typically about 50 mV with 0 DC bias.

The interdigitated electrodes 16 and the voltage source 22 are interconnected to form a circuit 24. The impedance sensor 12 also includes a window 26, typically fabricated from quartz, that overlays the interdigitated electrodes 16. A composition of material 28 is disposed between the interdigitated electrodes 16 and the window 26. The composition of material 28 is generally a liquid (although solid or gaseous materials may also be used). Examples of fluids that may be evaluated are biomedical fluids (such as hematology or urinary samples), organic dielectric fluids (such as oils), refrigerants, electro-chemical fluids (such as battery fluids), and industrial process fluids that may be evaluated to measure the health of operating machinery. An example of a solid material that may be evaluated is a thin film electrical material. The composition of material 28 is in contact with the interdigitated electrodes 16 and acts as a dielectric material that changes the capacitance of the circuit 24 compared with the capacitance of the circuit 24 without the composition of material 28 being present. An instrument system 30 is provided as part of the impedance sensor 12 to measure the impedance of circuit 24 as the voltage source establishes a voltage and a frequency across the circuit 24. Typically the voltage source 22 sweeps a range of frequencies and the instrument system 30 measures the impedance of the circuit 24 as the frequency changes. These measurements are referred to herein as electrical impedance spectroscopy (EIS) measurements.

Most embodiments of an apparatus 10 for evaluating a composition of material include a source of optical stimulation 32 that is configured to illuminate the composition of material 28 during at least a portion of the EIS measurement process. The source of optical stimulation 32 typically provides illumination (i.e., radiated light) having one or more wavelengths ranging from about 40 nm to about 1 millimeter. A typical source of optical stimulation operates in the ultraviolet regime, with wavelengths typically ranging from about 300 to about 400 nm. Typically the source of optical stimulation 32 is configured to provide different intensity levels of illumination, generally ranging from a few mW/cm$^2$ to a few W/cm$^2$. About 100 mW/cm$^2$ is a typical illumination intensity. In some embodiments the source of optical stimulation 32 may comprise a tunable laser or a plurality of lasers that may be adjusted or switched to provide two or more discreet wavelength bands or ranges of wavelengths. In some embodiments the source of optical stimulation 32 may produce monochromatic light that sweeps across a range of wavelengths over time.

A control system 34 is generally provided as part of the apparatus 10 for evaluating a composition of material. The control system 34 is generally configured to switch the source of optical stimulation 32 between the at least two states of illumination. "States of illumination" include (a) substantially no optical stimulation, (b) substantial optical stimulation, (c) optical stimulation at a first wavelength of light, (d) optical stimulation at a second wavelength of light, (e) a first level of light intensity, and (f) a second level of light intensity. The term "no optical stimulation" refers to an environment where the composition of material is exposed either to no ambient light or to a level of ambient light that is used to establish a baseline impedance measurement using the impedance sensor 12, 40 (FIG. 2), or 50 (FIG. 3). The term "substantial optical stimulation" refers to a level of light intensity that measurably changes the impedance of a composition of material. In some embodiments such stimulation may be sufficient to cause an energy level excitation in the composition of material. The terms "wavelength of light" refers to particular wavelengths or ranges of wavelength of light. The term intensity of light refers to a level of light intensity that is typically measured in mW/cm$^2$ or W/cm$^2$.

The control system 34 is generally also configured to activate the voltage source 22 and to use the instrument system 30 to measure the impedance of the composition of material 28 at each of the at least two states of illumination. In most embodiments, the control system 34 is further configured to cause the voltage source 22 to change frequencies between two or more frequencies or to sweep through a range of frequencies. In some embodiments the control system 34 may direct the source of optical stimulation 32 to scan a range of wavelengths while directing the voltage source 22 to maintain a constant frequency, during which time the instrument system 30 measures the impedance of the composition of material 28. Measurements of such electrical properties may be a surrogate for measurements of optical properties that are difficult or impossible to measure.

FIG. 2 illustrates an embodiment of a impedance sensor 40 that includes two capacitive plates 42 and an optical fiber 44 to deliver optical stimulation to a liquid specimen 46 that is disposed between the two capacitive plates 42. Yet another embodiment of an impedance sensor 50 is shown in FIG. 3, wherein two capacitive plates 52 are formed with at least one of the capacitive plates being a transparent conductor 54, such as indium-tin-oxide, deposited onto a transparent substrate, such as a quartz window. This embodiment allows a liquid specimen 56 between the two capacitive plates 52 to be exposed to optical stimulation 58 through the transparent conductor 54.

During EIS measurements, the electrode and chemical sample arrangement may substantially match an equivalent circuit model 70 shown in FIG. 4A. In this circuit, Rs may be negligibly small and Rp typically changes measurably with the optical stimulation. In other EIS measurements the electrode and chemical sample arrangement may match one of the equivalent circuit models of FIGS. 4B-4E.

Figure 5:
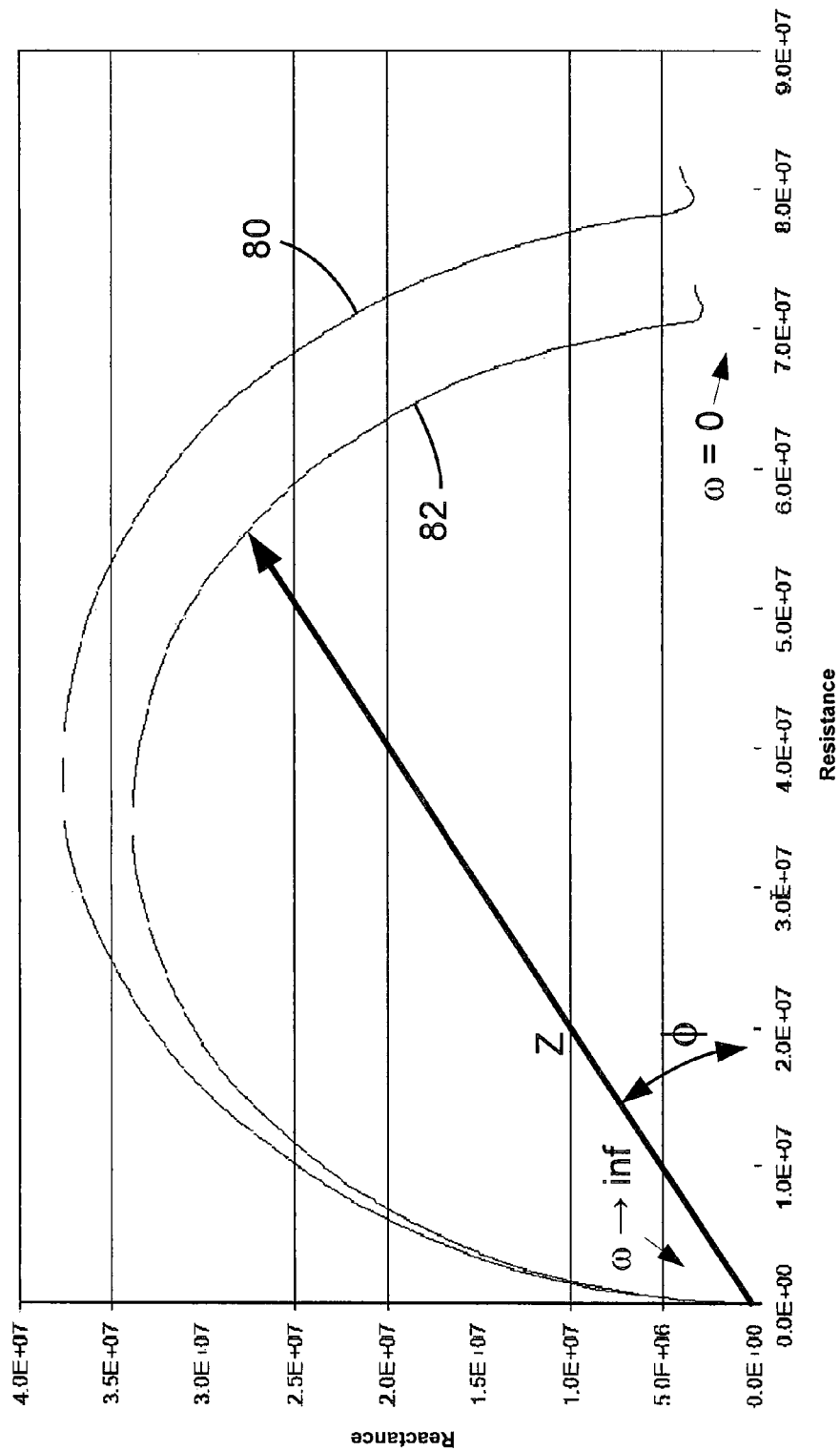
FIG. 5 presents Nyquist plots of averaged impedance measurements of four samples of engine oil under two test conditions.

FIG. 5 illustrates two Nyquist plots 80 and 82 that are typical of the types of EIS measurements that may be generated by the apparatus 10 of FIG. 1, or similar apparatuses using an alternate sensor such as impedance sensor 40 of FIG. 2 or impedance sensor 50 of FIG. 3. The plots 80 and 82 reflect equivalent circuits having a single time constant, such as the equivalent circuit 70 of FIG. 4A, and such circuits produce Nyquist plots having a single arch. Systems that match the equivalent circuits of FIGS. 4B-4D have two time constants, and the associated Nyquist plots will have two adjacent arches. The plot 80 represents the average measured impedance of four samples of fresh oil measured without substantial optical stimulation, and the plot 82 represents the average measured impedance of the four samples of fresh oil measured with substantial optical stimulation. Using plot 82 as an example, the impedance Z is measured by impedance sensor 12 (FIG. 1) as the frequency $\omega$ of voltage source 22 is varied from approximately 0 (direct current) to a very high frequency ($\omega \to \infty$). The angle between the impedance Z and the abscissa is commonly referred to as the phase angle $\phi$. Referring to the equivalent circuit model 70 of FIG. 4A, when the voltage source 22 approaches a DC value (i.e., $\omega \approx 0$) the capacitor C is an open circuit and substantially all of the current flows through Rp and Rs. If $\omega$ is approximately zero and Rs is negligibly small then the impedance of the equivalent model circuit is substantially established by the resistance value of Rp. When the voltage source 22 provides a very high frequency signal (in the kilo/megahertz range) the capacitor C is substantially a pure conductor and, if Rs is negligibly small, the impedance of the equivalent circuit is approximately zero. In some embodiments of an apparatus 10 for evaluating a composition of material, Z may be measured at just one phase angle φ. In some embodiments Z may be measured at two or more phase angles φ. In some embodiments Z may be measured over one or more ranges of phase angles φ. In some embodiments Z may be measured by configuring the voltage source 22 (in FIGS. 1 and 4) as a DC voltage source and measuring the resistance of the impedance sensor (12, 40, or 50).

Typically Nyquist plots are prepared for a composition of material under two different states of illumination, with examples of different "states of illumination" being previously described. FIG. 5 illustrates a characteristic that is typical for many compositions of material measured by a system for analyzing a composition of material using an impedance sensor system. This characteristic is that substantial optical stimulation typically reduces the impedance measured by the system compared with a baseline impedance measurement across a wide range of frequencies. Specifically in the case of the measurements presented in FIG. 5, impedance (Z) values in plot 82 (representing impedance measurements with substantial optical stimulation) are lower than the impedance (Z) values in plot 80 (representing baseline impedance) at every value of φ.

Figure 6:
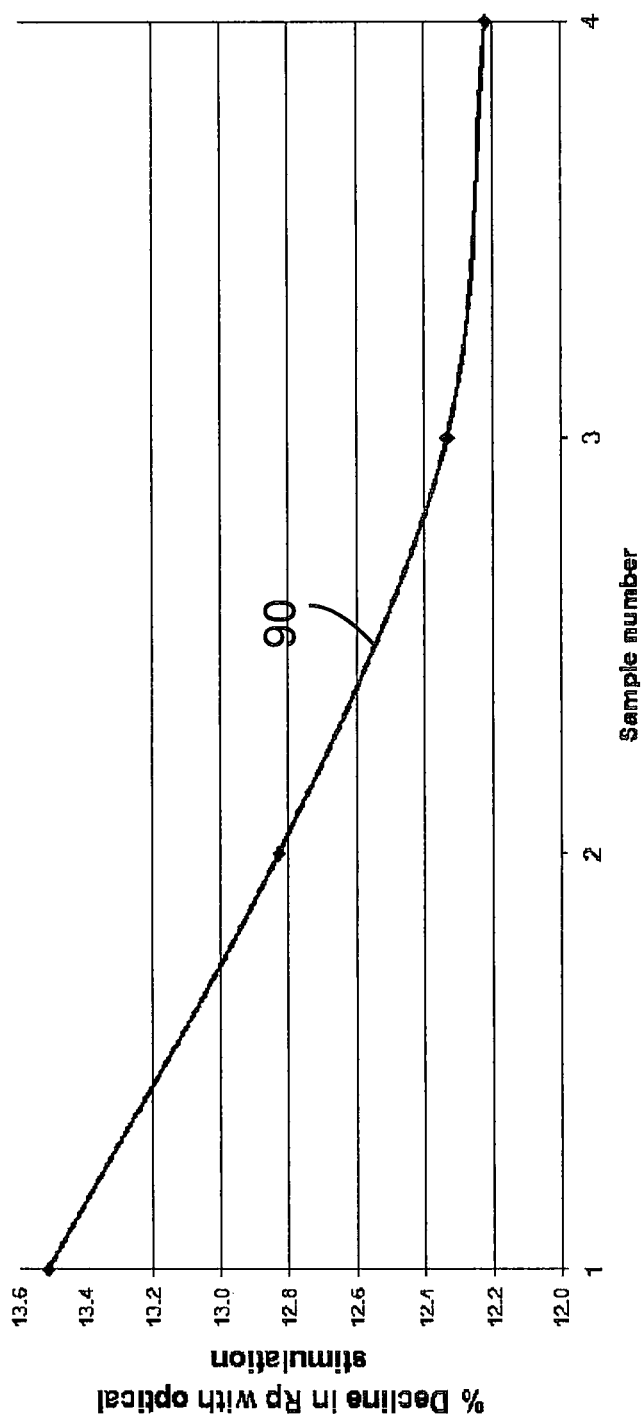
FIG. 6 is a plot of percent decline in measured impedance for four oil samples from a condition of substantially no optical stimulation to substantial optical stimulation.

FIG. 6 illustrates a plot 90 showing the difference between impedances measured (1) under substantial optical stimulation and (2) under substantially no optical stimulation, for four used oil samples. These used oil samples were acquired sequentially from an operating engine as the number of hours of operation increased over time, with sample 1 being the freshest sample and sample 4 being the sample that was in the engine for the longest time-in-service interval. FIG. 6 illustrates another characteristic that is typical for many compositions of material measured by a system for analyzing a composition of material using an impedance sensor (such as impedance sensor 12, 40 or 50). This characteristic is that the difference between impedances measured (1) under substantial optical stimulation and (2) under substantially no optical stimulation, typically varies monotonically with variations in chemical properties. In the case of the four oil samples of FIG. 6, the difference between impedances measured (1) under substantial optical stimulation and (2) under substantially no optical stimulation decreases as a function of the time in service of the oil.

Plot 90 of FIG. 6 is an example of a "reference impedance differential standard" that may be used in an apparatus 10 for evaluating a composition of material. That is, in some embodiments the control system 34 (FIG. 1) includes an analysis system that compares the impedance of the composition of material at each of at least two states of optical stimulation and uses a reference impedance differential standard (such as plot 90) to calculate a characteristic of the composition of material. If, for example, sample 2 in FIG. 6 represents oil having time-in-service of 1000 hours and sample 3 represents oil having time-in-service of 2000 hours, and if a new sample of oil is measured using the same apparatus and the percent decline in Rp with substantial optical stimulation is calculated at about 12.6%, then the analysis system may use plot 90 as a reference impedance differential standard to estimate that the time-in-service of the new sample of oil is between 1000 and 2000 hours.

EXAMPLES

An experimental test setup was used to evaluate samples of fresh engine oil and fresh diesel fuel (referred to herein as "neat" samples) as well as stock samples of engine oil containing approximately 1% and 10% fuel mixed in the oil. Four used engine oil samples were also tested. The test setup included a SOLARTRON™ 1296 Dielectric Interface with 1260 Frequency Response Analyzer. The impedance sensor system that was used for the measurements was an interdigited electrode with approximately 25 mm×30 mm active area consisting of 200 micron wide traces with a center-to-center spacing of 330 microns. The oil samples were placed onto the surface of the electrode and a quartz plate (2 mm thick) was lowered onto the sample. Shims of approximately 125 microns were used between the quartz and the electrode circuit to provide a uniform thickness for each sample. A high-intensity mercury arc lamp (ELECTROLITE™ ELC-410 UV adhesive curing gun) was used to optically stimulate the samples.

Figure 7:
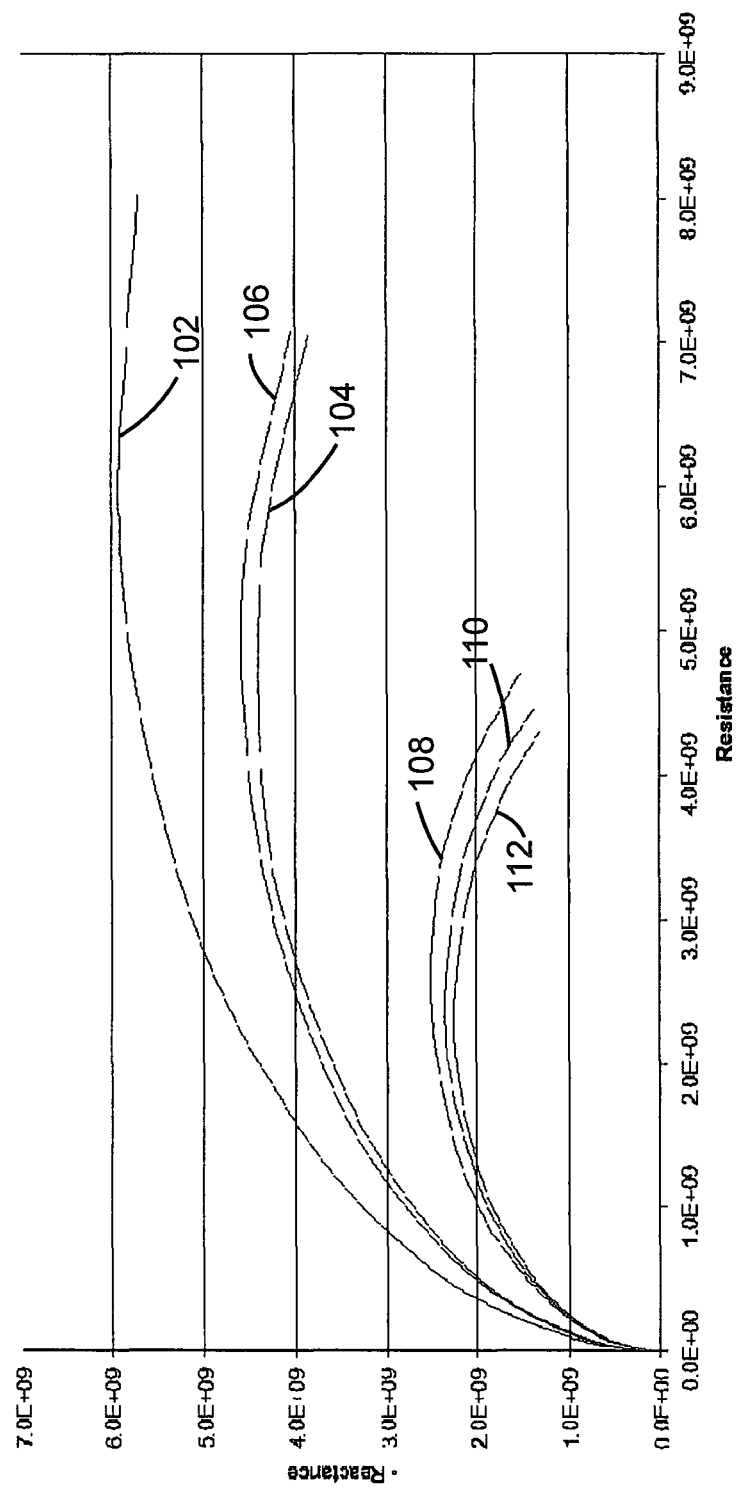
FIG. 7 presents Nyquist plots of impedance of diesel fuel samples without optical stimulation.
Figure 8:
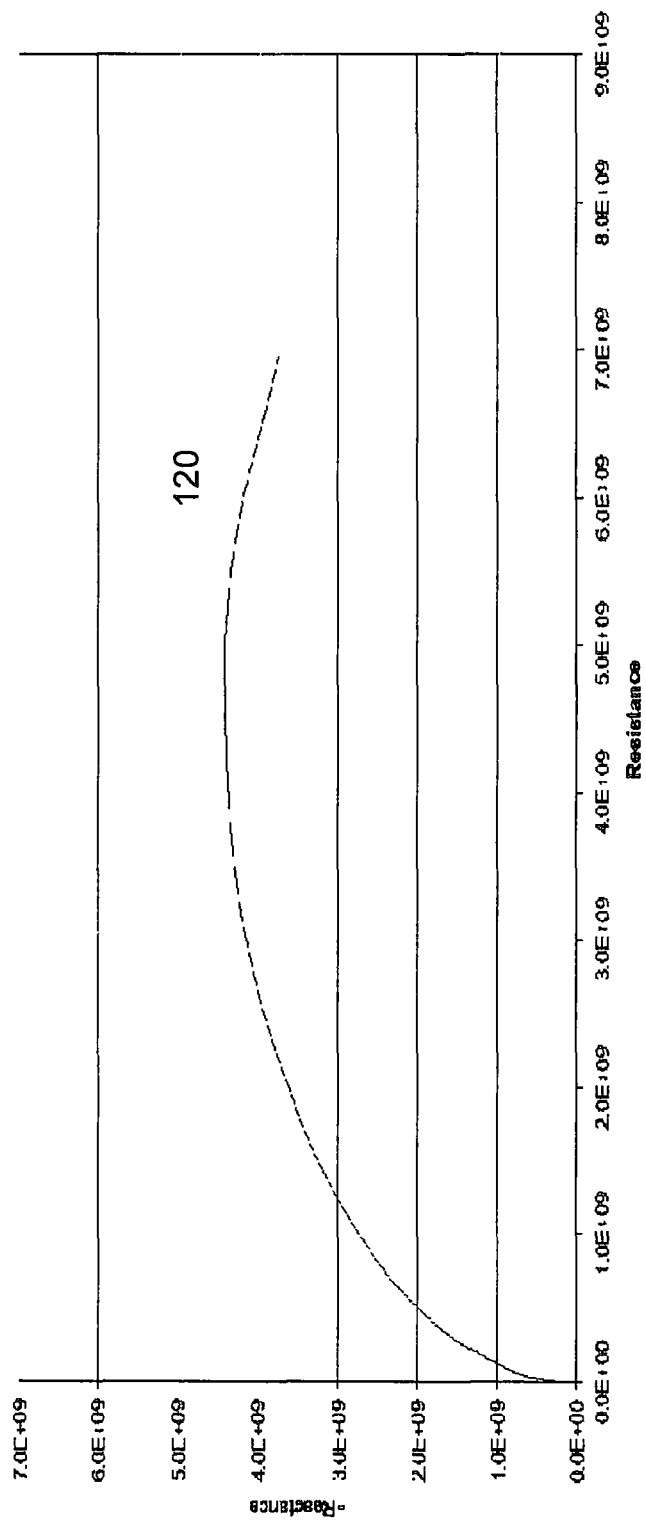
FIG. 8 presents a Nyquist plot of impedance of diesel fuel with optical stimulation.

In a first set of experiments, several measurements were made on neat diesel fuel samples. The test sample was changed three times to evaluate repeatability. In FIG. 7, traces 102, 104 and 106 represent impedance measurements of the three test samples. Traces 108, 110 and 112 were all obtained from a single sample but at intervals of about 4 minutes between the measurements. As illustrated in FIG. 7, significant variation was observed in the Nyquist plot impedance measurements both between samples and with the same sample tested at different times. FIG. 8 illustrates a Nyquist plot 120 of a neat oil sample measured while the sample was under substantial optical stimulation. Plot 120 illustrates that this optical stimulation did not yield a change in the impedance outside the range of variability in the baseline scans (shown in FIG. 7). As used here the term "baseline scan" refers to a Nyquist plot made under conditions of substantially no optical stimulation.

Figure 9:
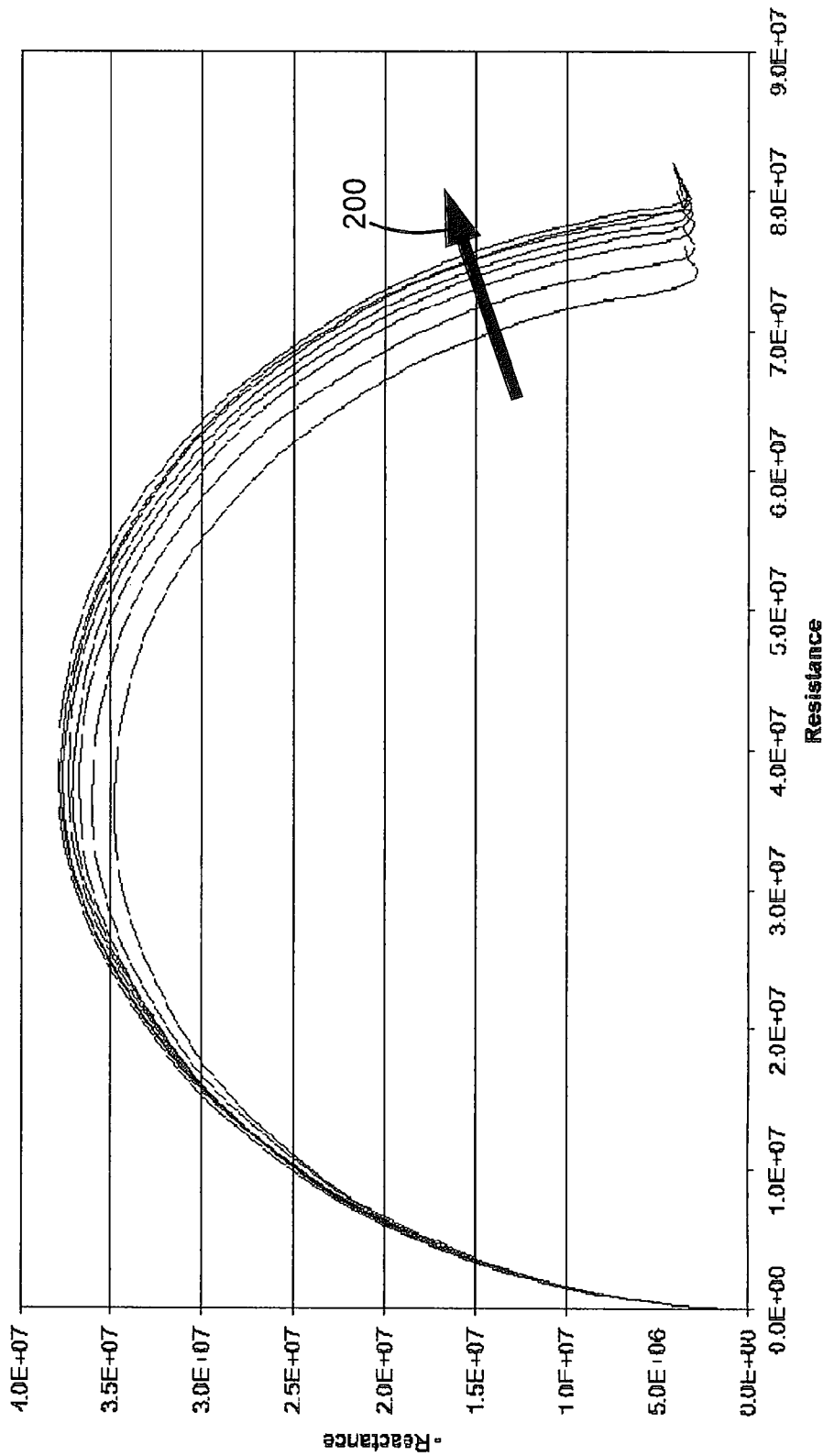
FIG. 9 presents Nyquist plots of repeated impedance measurements of an engine oil sample.

FIG. 9 illustrates a series of Nyquist plots of impedance measurements made on a neat engine oil sample to evaluate the repeatability of scans. The data in FIG. 9 illustrates significant variation, although the variation became smaller as the sample stabilized over time (the direction of arrow 200).

Figure 10:
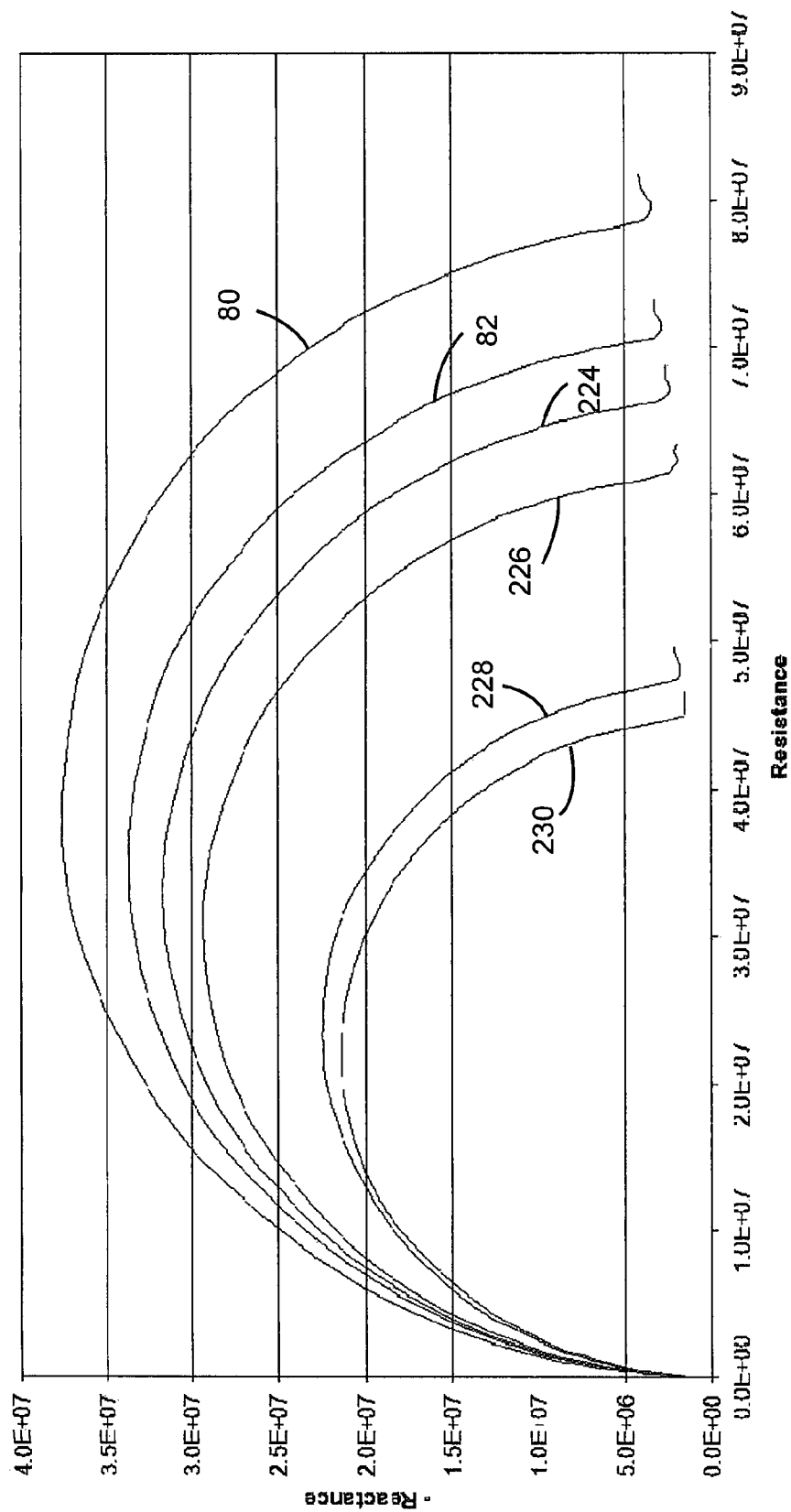
FIG. 10 presents Nyquist plots of impedance of three materials of composition each measured under two different conditions.

FIG. 10 illustrates results from scanning stock samples of 1% and 10% fuel in oil to obtain baseline and optically stimulated data. Averaged data sets are compared with neat oil data. Traces 80 and 82 are the same traces for the baseline and for the substantially optically stimulated conditions respectively that were presented in FIG. 5 and discussed previously. Trace 224 is a baseline trace for a mixture of 1% fuel in oil and trace 226 is the corresponding trace of that sample under substantial optical stimulation. Trace 228 is a baseline trace for a mixture of 10% fuel in oil and trace 230 is the corresponding trace of that sample under substantial optical stimulation. FIG. 10 illustrates that optical stimulation reduces the impedance of all of the samples containing oil. In the stock samples the trend was that the presence of diesel fuel lowered the impedance of the mixture. This is counter-intuitive, given that the impedance of the fuel itself was two orders of magnitude higher than that of the oil samples. It should be noted that data for baseline and optically stimulated neat fuel were inconclusive, and those data are not presented.

Figure 11:
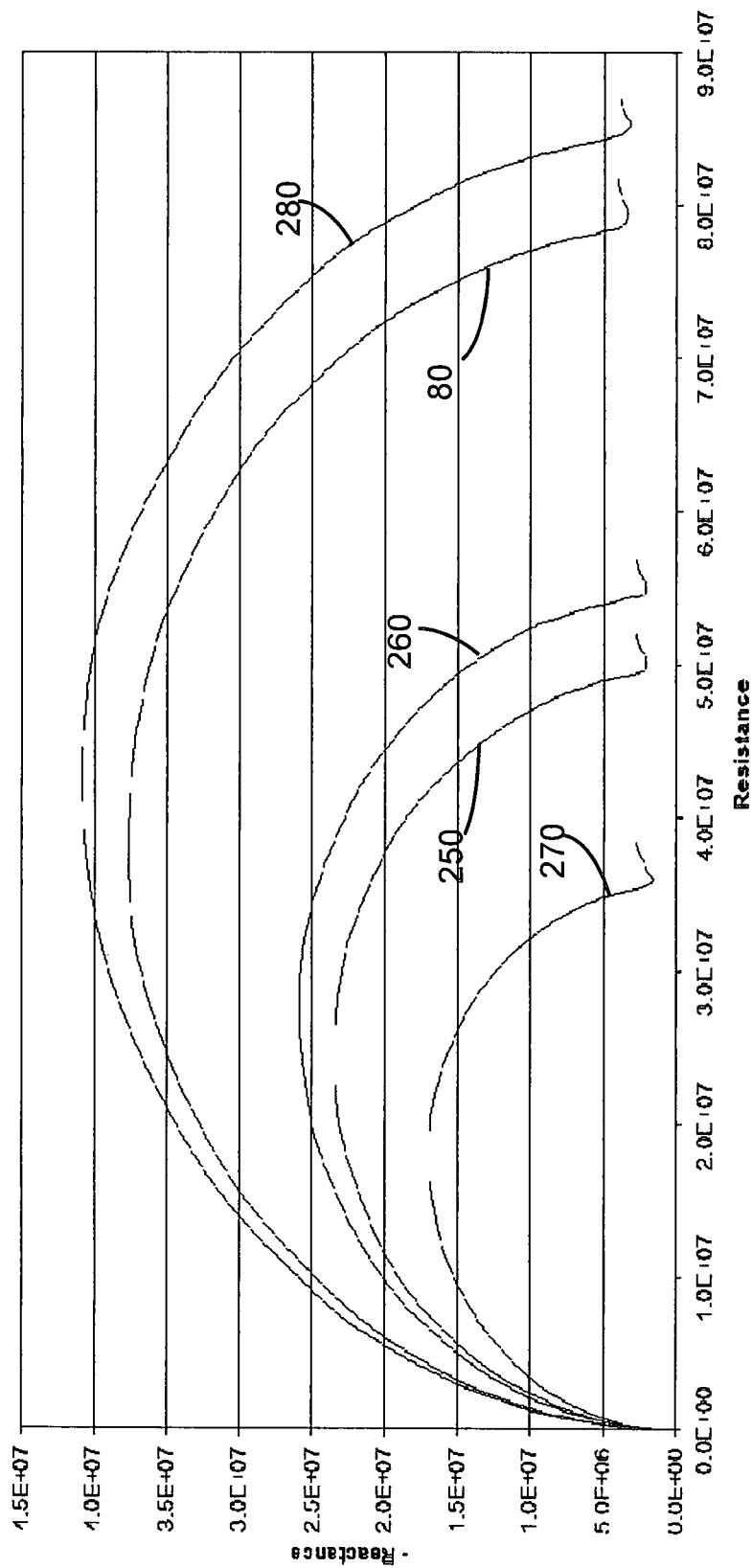
FIG. 11 presents Nyquist plots of impedance of four samples of used oil and one neat oil sample, all measured without substantial optical stimulation.

As previously discussed with respect to FIG. 6, four used oil samples were measured to determine the variation in impedance between them and to evaluate the influence of optical stimulation on the impedance. Sample 1 was the first sample taken and represented the shortest time in service. Sample 2 was taken second, sample 3 taken third, and sample 4 taken last and represented the longest time in service. Baseline data for these samples and the neat oil sample are presented in FIG. 11. As in previous examples, trace 80 represents the data from baseline measurements of neat oil. Trace 250 represents baseline data from used oil having the shortest time in service (sample 1). Trace 260 represents baseline data from sample 2, trace 270 represents baseline data from sample 3, and trace 280 represents data from sample 4. Some monotonic variation in the samples was anticipated, and the variation in impedance was observed to be generally increasing among the four samples. However, sample 3 (trace 270) was an exception. It should be noted that sample 3 demonstrated inconsistent behavior in other optically-based measurements (not reported here) that were performed on the set of four used oil samples. Another anomaly in the data is that the impedance of sample 4 (trace 280) exceeds that of the neat oil sample (trace 80). Other methods of investigation utilizing comparisons of scalar impedance measurements also yielded non-monotonic data.

Figure 12:
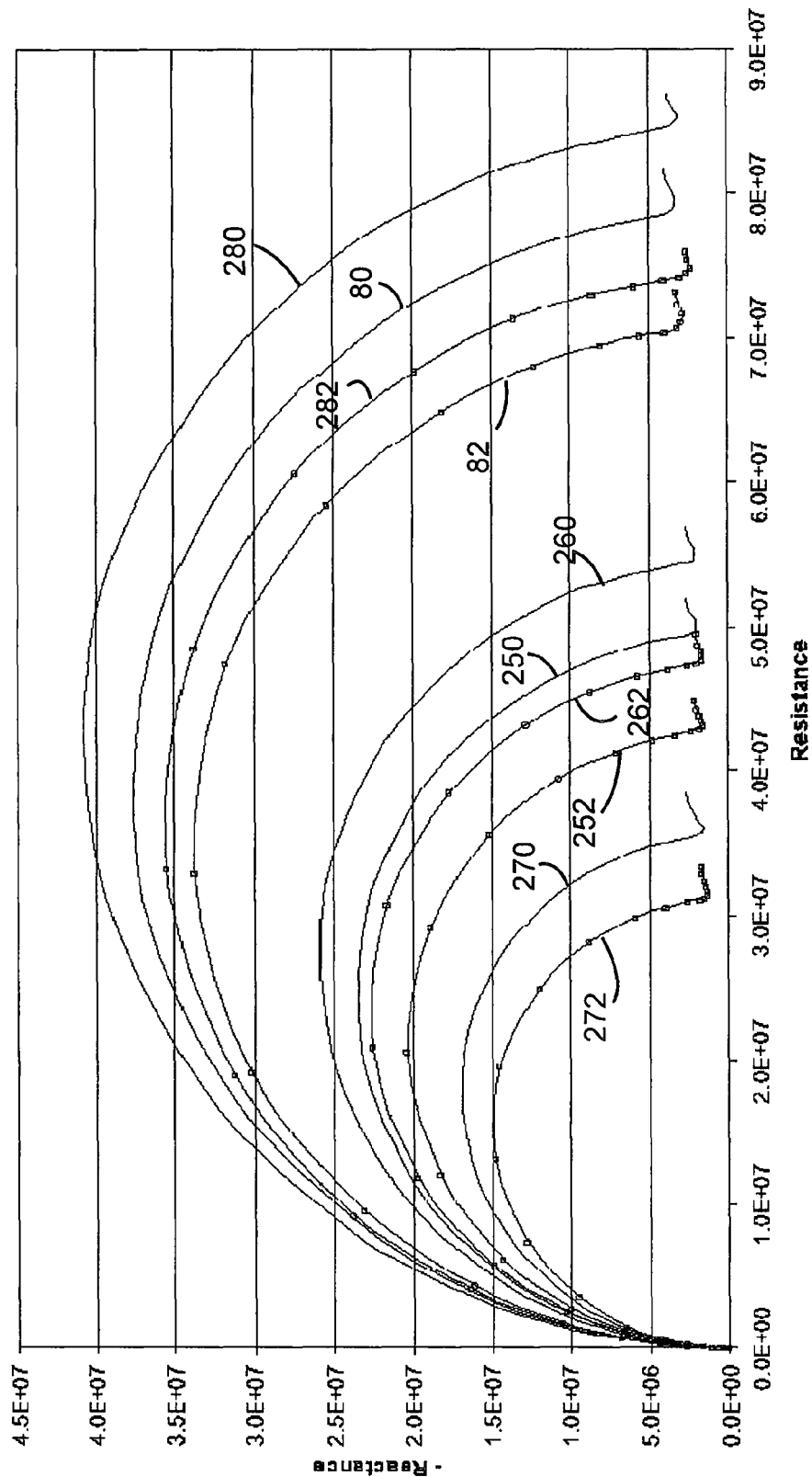
FIG. 12 presents Nyquist plots of impedance of four samples of used oil and one neat oil sample, measured under two conditions of optical stimulation.

In contrast, FIG. 12 illustrates the benefit of differential impedance measurements. Traces 252, 262, 272, and 282 represent measurements taken of used oil samples 1, 2, 3, and 4 respectively, each under substantial optical stimulation. In each case the impedance measured under substantial optical stimulation is less than the baseline impedance measurements. Furthermore, the differential measurements are the data plotted and previously presented in FIG. 6, which illustrate that the difference between impedances measured (1) under substantial optical stimulation and (2) under substantially no optical stimulation typically varies monotonically with variations in chemical properties (i.e., the difference decreases as a function of the time in service of the oil).

Figure 13:
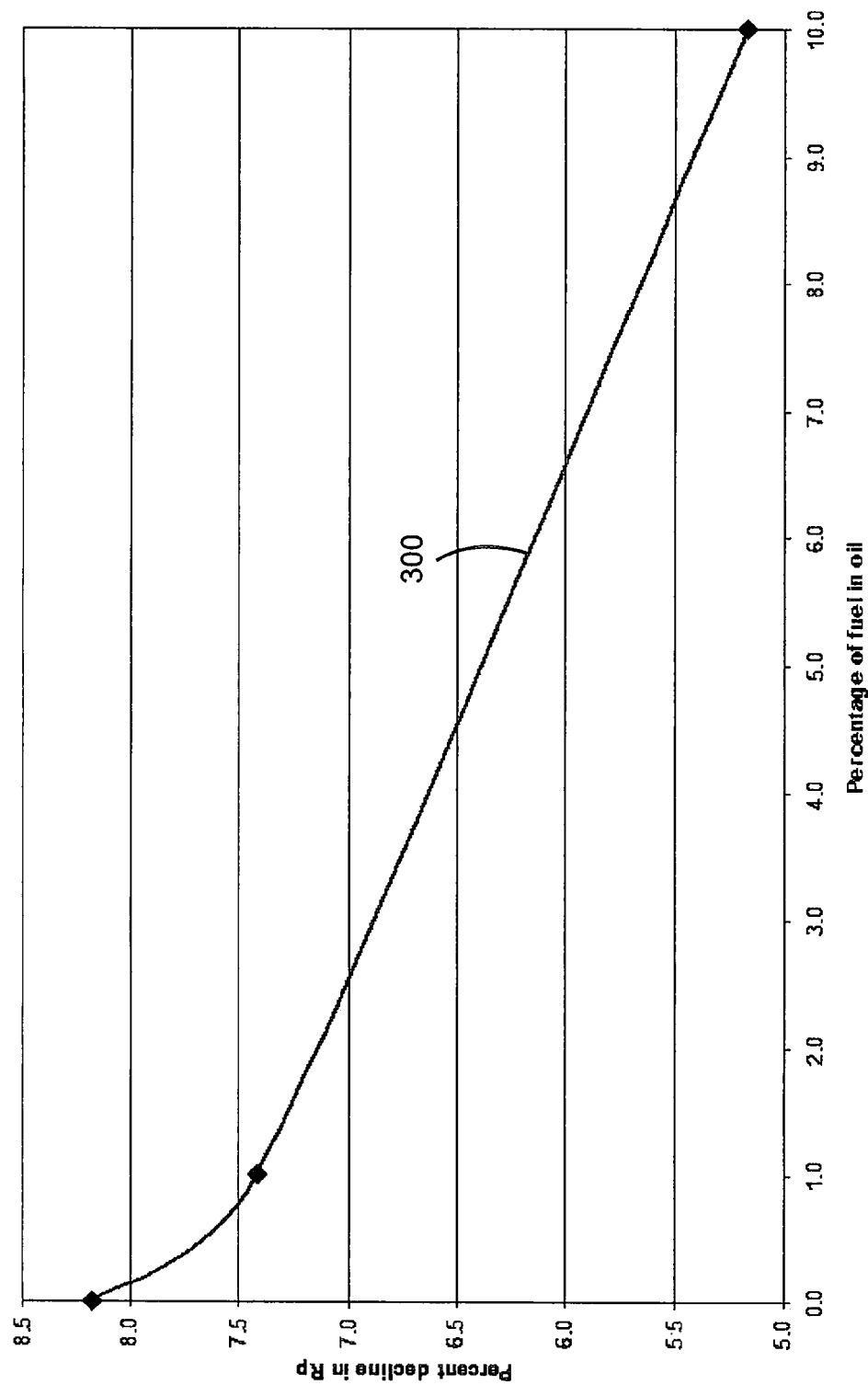
FIG. 13 is a plot of percent decline in measured impedance for oil in fuel samples from a condition of substantially no optical stimulation to substantial optical stimulation.

FIG. 13 illustrates the percentage change in the value of Rp that was measured (1) under substantial optical stimulation and (2) under substantially no optical stimulation for the stock oil samples consisting of the neat oil as well as the 1% and 10% fuel in oil. The percentage change in Rp is observed to decrease with increasing fuel content. Consequently, trace 300 in FIG. 13 may be used as a reference impedance differential standard for estimating the percent of fuel in oil in a manner similar to the way trace 90 in FIG. 6 was described for use as a reference impedance differential standard for estimating the life in service of oil.

In summary, embodiments disclosed herein provide various methods and apparatuses for evaluating a composition of material. The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. A method of evaluating a fluid material selected from the group consisting of: biomedical fluids, organic dielectric fluids, refrigerants, electrochemical fluids, and industrial process fluids comprising:
   measuring a first electrical impedance of the fluid material at one or more frequencies greater than 65 kHz under a first state of illumination;
   measuring a second electrical impedance of the fluid material at one or more frequencies greater than 65 kHz under a second state of illumination that is different from the first state of illumination;
   and evaluating the fluid material based upon a difference between the first electrical impedance and the second electrical impedance.

2. The method of claim 1 wherein the first state of illumination is substantially no optical stimulation and the second state of illumination is substantial optical stimulation.

3. The method of claim 1 wherein the first state of illumination comprises optical stimulation at a first wavelength of light that causes an energy level excitation in the fluid material.

4. The method of claim 1 wherein the first state of illumination comprises optical stimulation at a first wavelength of light and the second state of illumination comprises optical stimulation at a second wavelength of light that is different from the first wavelength of light.

5. The method of claim 1 wherein the first state of illumination comprises substantial optical stimulation at a first light intensity and the second state of illumination comprises substantial optical stimulation at a second light intensity that is different from the first light intensity.

6. The method of claim 1 wherein the step of measuring a first electrical impedance comprises measuring a plurality of first electrical impedances over a frequency range, the step of measuring a second electrical impedance comprises measuring a plurality of second electrical impedances over the frequency range, and the step of evaluating the fluid material comprises evaluating a plurality of differences between the measurements of the first electrical impedances over the frequency range and the measurements of the second electrical impedances over the frequency range.

7. The method of claim 1 wherein the step of evaluating the fluid material comprises comparing the difference between the first electrical impedance and the second electrical impedance with a reference impedance differential standard.

8. The method of claim 1 wherein the fluid material comprises oil, wherein the first state of illumination is substantially no optical stimulation and the second state of illumination is substantial optical stimulation, and wherein the step of evaluating the fluid material comprises determining that the second electrical impedance is different from the first electrical impedance by an impedance differential, and comparing the impedance differential with a reference impedance differential standard to estimate how long the oil has been in service.

9. An apparatus for evaluating a fluid material selected from the group consisting of: biomedical fluids, organic dielectric fluids, refrigerants, electrochemical fluids, and industrial process fluids comprising:
   an impedance sensor system configured to measure impedance of the fluid material at one or more frequencies greater than 65 kHz;
   a source of optical stimulation configured to expose the fluid material to at least two different states of illumination; and
   a control system configured to:
   (1) switch the source of optical stimulation between the at least two different states of illumination, and
   (2) trigger the impedance sensor system to measure the impedance of the fluid material at each of the at least two different states of illumination.

10. The apparatus of claim 9 wherein the at least two different states of illumination comprise (1) substantially no optical stimulation and (2) substantial optical stimulation.

11. The apparatus of claim 9 wherein the at least two different states of illumination comprise optical stimulation at a wavelength of light that causes an energy level excitation in the fluid material.

12. The apparatus of claim 9 wherein the at least two different states of illumination comprise (1) optical stimulation at a first wavelength of light and (2) optical stimulation at a second wavelength of light.

13. The apparatus of claim 9 wherein the at least two different states of illumination comprise (1) optical stimulation at a first light intensity and (2) optical stimulation at a second light intensity.

14. The apparatus of claim 9 wherein the impedance sensor comprises a capacitive probe.

15. The apparatus of claim 9 wherein the source of optical stimulation comprises an optical fiber.

16. The apparatus of claim 9 wherein the source of optical stimulation comprises a light source for providing light at a wavelength and the at least two different states of optical stimulation comprise optical stimulation at the wavelength of light and the apparatus further comprises a test port window that is at least partially transparent to the light at the wavelength and that is disposed at least partially between at least a portion of the fluid material and the light source.

17. The apparatus of claim 9 further comprising an analysis system to compare the impedance of the fluid material at each of the at least two different states of optical stimulation and calculate a characteristic of the fluid material based at least in part on the comparison.

18. An apparatus for evaluating a fluid material selected from the group consisting of: biomedical fluids, organic dielectric fluids, refrigerants, electrochemical fluids, and industrial process fluids comprising:

an impedance sensor system configured to measure impedance of the fluid material, the impedance sensor system including a pattern of interdigitated electrodes disposed on a printed circuit board;

a source of optical stimulation configured to expose the fluid material to at least two different states of illumination;

a control system configured to:
(1) switch the source of optical stimulation between the at least two different states of illumination, and
(2) trigger the impedance sensor system to measure the impedance of the fluid material at each of the at least two different states of illumination; and a test port window that is at least partially transparent to the optical stimulation, the test port window having a surface that is disposed adjacent and substantially parallel to the printed circuit board, wherein the fluid material is disposed between and in contact with the printed circuit board and the surface of the test port window.

19. A method for evaluating oil used for lubrication comprising:

measuring a first electrical impedance of the oil while exposing the oil to substantially no optical stimulation;

measuring a second electrical impedance of the oil while exposing the oil to substantial optical stimulation;

determining that the second electrical impedance is different from the first electrical impedance by an impedance differential; and comparing the impedance differential with a reference impedance differential standard to estimate how long the oil has been in service.

\* \* \* \* \*